US007659450B2

(12) United States Patent
Cahoon et al.

(10) Patent No.: US 7,659,450 B2
(45) Date of Patent: Feb. 9, 2010

(54) LCB1 SUBUNIT OF SERINE PALMITOYLTRANSFERASE

(75) Inventors: Rebecca E. Cahoon, Webster Grove, MO (US); Anthony J. Kinney, Wilmington, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 402 days.

(21) Appl. No.: 10/309,629

(22) Filed: Dec. 4, 2002

(65) Prior Publication Data

US 2003/0166145 A1 Sep. 4, 2003

Related U.S. Application Data

(63) Continuation-in-part of application No. 09/665,842, filed on Sep. 20, 2000, now abandoned, which is a continuation of application No. PCT/US99/06045, filed on Mar. 19, 1999.

(60) Provisional application No. 60/079,430, filed on Mar. 26, 1998.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. ...................... 800/298; 536/23.1; 536/23.6; 435/320.1; 435/410; 435/419; 800/278

(58) Field of Classification Search ................. 536/23.1, 536/23.6; 435/468, 410, 419, 320.1; 800/278, 800/287, 290, 298
See application file for complete search history.

(56) References Cited

U.S. PATENT DOCUMENTS 5,583,030 A 12/1996 Dickson et al.

FOREIGN PATENT DOCUMENTS

WO     WO 99/49053    *    9/1999

OTHER PUBLICATIONS

Bowie et al, Science 247:1306-1310, 1990.*
McConnell et al, Nature 411 (6838):709-713, 2001.*
Kano-Murakami et al (1993, FEBS 334:365-368).*
Buede et al (1991, Journal of Bacteriology, July:4325-4332).*
Hanada et al (1997 J. Biological Chemistry 272:51 32108-32114).*
Hanada et al (1997, The Journal of Biological Chemistry 272(51):32108-32114).*
Brenner, Errors in genome annotation, Apr. 1999, TIG, vol. 15, No. 4, pp. 132-133.*
Doerks et al., Protein annotation detective work for function prediction, Jun. 1998, TIG, vol. 14, No. 6, pp. 248-249.*
Tamura et al., Characterization of an Arabidopsis cDNA Encoding a Subunit of Serine . . . , 2001, Plant Cell Physiol, vol. 42, No. 11, pp. 1274-1281.*
Finnega et al., Transgene Inactivation: Plants Fight Back!, Sep. 1994, Bio/Technology, vol. 12, pp. 883-887.*
Eshed et al., Establishment of polarity in lateral ograns of plants, 2001, Current Biology, vol. 11, pp. 1251-1260.*
Barioch, Go hunting in sequence database but watch out for the traps, Oct. 1996, TIG, vol. 12, No. 10, pp. 425-427.*
Smith et al., The challenges of genome sequence annotation or "The devil in the details", Nov. 1997, Nature Biotechnology, vol. 15, pp. 1222-1223.*
Bertram Weiss et al., Eur. J. Biochem., vol. 249:239.247,1997, Human and murine serine-palmitoyl-CoA transferase.
EMBL Sequence Data Library Accession No: Y08685, Oct. 4, 1997, Stoffel., W., Human and murine serine-palmitoyl-CoA transferase Cloning, expression and characterization of the key enzyme in sphingolipid synthesis.
EMBL Sequence Data Library Accession No: X95641, Oct. 23, 1997, Weiss, B. et al., Human and murine serine-palmitoyl-CoA transferase Cloning, expression and characterization of the key enzyme in sphingolipid synthesis.
Kentaro Hanada et al., Journ. of biol. Chem., vol. 272(51):32108-32114, 1997, A Mammalian Homoiog of the Yeast LCB1 Encodes a Component of Serine Palmitoyltransferase, the Enzyme Catalyzing the First Step in Sphingolipid Synthesis.
EMBL Sequence Data Library Accession No: AF004831, Dec. 16, 1997, Hanada, K. et al., , A Mammalian Homolog of the Yeast LCB1 Encodes a Component of Serine Palmitoyltransferase, the Enzyme Catalyzing the First Step in Sphingolipid Synthesis.
EMBL Sequence Data Library Accession No: AF003823, Feb. 11, 1998, Hanada, K. et al., A mammalian homolog of the yeast LCB1 encodes a component of serine palmitoyltransferase, the enzyme catalyzing the first step in sphingolipid synthesis.
EMBL Sequence Data Library Accession No: Z99708, Oct. 2, 1997, Bevan, M. et al.
EMBL Sequence Data Library Accession No: D46698, Mar. 8, 1995, Sasaki, T. et al., Rice cDNA from shoot.
EMBL Sequence Data Library Accession No: AA750817, Jan. 21, 1998, Nahm, B.H. et al., Large-scale Sequencing Analysis of ESTs from Rice Immature Seed.
EMBL Sequence Data Library Accession No: D39197, Nov. 13, 1994, Sasaki, T. et al., Rice cDNA from root.
Suzanne M. Mandala et al., Journ. of Antibiotics, vol. 50(4):339-343, 1999, Viridlofungins, Novel inhibitors of Sphingolipid Synthesis.

(Continued)

*Primary Examiner*—Stuart F. Baum

(57) ABSTRACT

This invention relates to an isolated nucleic acid fragment encoding a serine palmitoyltransferase Lcb1 subunit. The invention also relates to the construction of a chimeric gene encoding all or a portion of the serine palmitoyltransferase Lcb1 subunit, in sense or antisense orientation, wherein expression of the chimeric gene results in production of altered levels of the serine palmitoyltransferase Lcb1 subunit in a transformed host cell.

11 Claims, 3 Drawing Sheets

OTHER PUBLICATIONS

Kentaro Hanada et al., Journ. of Biol. Chem., A Mammalian Homolog of the Yeast LCB1 Encodes a Component of Serine Palmitoyltransferase, the Enzyme Catalyzing the First Step in Sphingolipid Synthesis, vol. 272(31):32108-32114, 1997.

National Center for Biotechnology Information General Identifier No. Z99708, Dec. 11, 1998.

National Center for Biotechnology Information General Identifier No. 4006914, Dec. 11, 1998.

National Center for Biotechnology Information General Identifier No. Y08685, Oct. 27, 1997.

Bertram Weiss et al., Human and murine serine-palmitoyl-CoA transferase, Eur. J. biochem., vol. 249:239-247, 1997.

Rebecca Buede, et al., "Cloning and Characterization of LCB1, a Saccharomyces Gene Required for Biosynthesis of the Long-Chain Base Component of Sphingolipids", Journal of Bacteriology, Jul. 1991, p. 4325-4332, vol. 173, No. 14.

Williams, Robert D. et al., "Enzymology of Long-Chain Base Synthesis . . . ", Archives Of Biochemistry And Biophysics, vol. 228, No. 1, Jan. 1984, pp. 282-291.

Merrill, Alfred H. Jr., "Characterization Of Serine Palmitoyltransferase Activity . . . ", Biochimica et Biophysica Acta, 754(1983), pp. 284-291.

Hanada, Kentaro et al., "A Mammalian Homolog Of The Yeast . . . ", The Journal Of Biological Chemistry, vol. 272, No. 51, Issue of Dec. 19th, pp. 32108-32114, 1997.

Hanada, Kentaro et al., "A Temperature-Sensitive Mammalian . . . ", The Journal Of Biological Chemistry, vol. 265, No. 36, Issue of Dec. 25th, pp. 22137-22142, 1990.

Hanada, Kentaro et al., "Mammalian Cell Mutants . . . ", The Journal Of Biological Chemistry, vol. 273, No. 50, Issue of Dec. 11th, pp. 33787-33794, 1998.

Yasuda, Satoshi et al., "Localization, Topology, And Function . . . ", The Journal Of Biological Chemistry, vol. 278, No. 6, Issue of Feb. 7, pp. 4176-4183, 2003.

Buede, Rebecca et al., "Cloning And Characterization Of LCB1 . . . ", Journal Of Bacteriology, vol. 173, No. 14, pp. 4325-4332, Jul. 1991.

Hanada, Kentaro et al., "Purification Of The Serine . . . ", The Journal Of Biological Chemistry . . . , vol. 275, No. 12, Issue of Mar. 24, pp. 8409-8415, 2000.

Ikushiro, Hiroko et al., "A Water-Soluble Homodimeric . . . ", The Journal Of Biological Chemistry, vol. 276, No. 21, Issue of May 25, pp. 18249-18256, 2001.

* cited by examiner

Figure 1

```
SEQ ID NO:13    MASNL--VEMFNAALNWTMILESPSARVVLFGVPIRGHFFVEGLLGVVIIILLTRKSYK
SEQ ID NO:02    MDMALPVVNATTAVLARVSXAFNAPLARAVVFGVHIDGHLVVGRLLIAINVFQLSRKSYK
SEQ ID NO:04    ..................TRDFS------------GHLVVEGLLIAVIVFQLSRKSYK
SEQ ID NO:12    ..........................................................
                1                                                         60

SEQ ID NO:13    PPKRPLTEQEIDELCDEWVPEPLIPPTTEDMKHEPPVLESAAGPHTTVNGKDVVNFASAN
SEQ ID NO:02    PPKKPLTEKEIDELCDEWEPEPLCPPVKEGARIDTPMLESAAGPHTIVDGKEVVNFASAN
SEQ ID NO:04    PPKKPLTE----------------------------------SAAGPHTIVDGKEVVNFASAN
SEQ ID NO:12    ..........................................................
                61                                                        120

SEQ ID NO:13    YLGLIGHEKLLESCTSALEKYGVGSCGPRGFYGTIDVHLDCETRISKFLGTPDSILYSYG
SEQ ID NO:02    YLSLIGNEKIIDSCISSLEKYGVGSCGPCGFYGTTDVHLDCESKIAKFLGTPDSILYSYG
SEQ ID NO:04    YLSLIGNEKIIDSCISSLEKYGVGSCGPCGFYGTTDVHLDCESKIAKFLGTPDSILYSYG
SEQ ID NO:12    ..........................................................
                121                                                       180

SEQ ID NO:13    LSTMFSTIPCFCKKGDVIVADEGVHWGIQNGLQLSRSTIVYFKHNDMESLRITLEKIMTK
SEQ ID NO:02    ISTIFNVIPAFCKKKGDIIVADEGVHWAVTNGLHLSRSTVVYFKHNDMASLASTLEKLTRG
SEQ ID NO:04    ISTIFNVIPAFCKKKGDIIVADEGVHWAVTNGLHLSRSTVVYFKHNDMASLASTLEKLTRG
SEQ ID NO:12    ..........................................................
                181                                                       240
```

Figure 1 (Cont.)

```
SEQ ID NO:13   YKRSKNLRRYIVAEAVYQNSGQIAPLDEIVKLKEKYRFRVILDESNSFGVLGRSGRGLAE
SEQ ID NO:02   NKRAEKIRRYIVVESIYQNSGQIAPLDEIVRLKEKYRFRVILEESHSFGVLGKSGRGLAE
SEQ ID NO:04   NKRAEKIRRYIVVESIYQNSGQIAPLDEIVRLKEKYRFRVILEESHSFGVLGKSGRGLAE
SEQ ID NO:12   ...........QNSGQIAPLDEIVKLKEKYLFRVILEESHSFGVLGKSGRGLAE
                                                                        300
                                                                        241

SEQ ID NO:13   HHSVPIEKIDVVTAAMGHALATEGGFCTGNARIIDYQRLSSSGYVFSASLPPYLASAAIT
SEQ ID NO:02   HYGVPIEKIDIITAGMGNALATDGGFCTGSVRVVDHQRLSSSGYVFSASLPPYLATAAVS
SEQ ID NO:04   HYGVPVS------------------------------------------------------
SEQ ID NO:12   HYGVPIDKIDIITAGMGNALATDGGFCTGSARVVDHQRLSSAGYVFSASLPPYLASAAVS
                                                                        360
                                                                        301

SEQ ID NO:13   AIDVIDQNPDINAGN--------NAGLSDIKGMSLTSNRESPIVFLKLEKSSGSAKDDLLL
SEQ ID NO:02   AVNYLEQNPAVLANLRSNIALLHKELSDTPGLEIFSHVLSPIVFLKLKKSTGSPTTDLDL
SEQ ID NO:04   ----------------------------------------VWPQLFLMFHHNAPPVVSDRGA
SEQ ID NO:12   AVNYLEENPSVLANLRSNVALLHAGLSDAPGLEISSHALSPIVFLKKSTGLATDLDL
                                                                        420
                                                                        361

SEQ ID NO:13   LEKMADRALKEDSLLVVSSKRSFLDKCRLPVGIKLYVSAGHSESDLLKASESLKRLASEL
SEQ ID NO:02   LETIAGRVLKEDSVLIVTSKKSNLDRCKLPVGIRLFVSAGHTESDISRLSSSLKRVSAAV
SEQ ID NO:04   L--------LPSSQTRPNCLVKC----------LGQSGHQEWSHGTSAGHYKK......
SEQ ID NO:12   LETIAEQVLKEDSVFIVASKRSTLDRCKLPVGIRLFVSAGHTESDISKVCSSLKRISASV
                                                                        480
                                                                        421
```

Figure 1 (cont.)

```
SEQ ID NO:13    LLK..S
SEQ ID NO:02    LSDCF.
SEQ ID NO:04    ......
SEQ ID NO:12    LSDHV.
                481  486
```

LCB1 SUBUNIT OF SERINE PALMITOYLTRANSFERASE

This application is a continuation-in-part of U.S. application Ser. No. 09/665,842, filed Sep. 20, 2000, now abandoned, which is a continuation of International Application No. PCT/US99/06045, filed Mar. 19, 1999, which claims the benefit of U.S. Provisional Application No. 60/079,430, filed Mar. 26, 1998.

FIELD OF THE INVENTION

This invention is in the field of plant molecular biology. More specifically, this invention pertains to nucleic acid fragments encoding Lcb1 subunit of serine palmitoyltransferase in plants and seeds.

BACKGROUND OF THE INVENTION

Sphingolipids are abundant components of the plasma membrane of higher eukaryotes. Specific sphingolipids are produced via the addition of polar groups to the 1-hydroxyl group of ceramide. The mechanism of de novo synthesis of ceramide in plants begins with the condensation of serine and palmitoyl-CoA to yield 3-ketosphinganine. This reaction is catalyzed by serine palmitoyltransferase (SPT; EC 2.3.1.50). Further reactions convert 3-ketosphinganine to ceramide. Serine palmitoyltransferase is thought to have at least two subunits, Lcb1 and Lcb2, with Lcb1 containing a conserved non-functional pyridoxal binding site which does not have the essential lysine residue.

Sphingolipids appear to play essential roles in cellular events such as proliferation, senescence, differentiation, apoptosis and response to desiccation stress. Although not much is known about the mechanism of this pathway, it has been suggested that SPT is the rate-limiting step in the production of ceramide. The genes encoding the Lcb1 subunit of SPT have been isolated from human, mouse and *Saccharomyces cerevisiae*. All of these genes appear to contain a putative transmembrane domain and are probably localized at the endoplasmic reticulum (Hanada, K. et al. (1997) *J Biol Chem* 272:32108-32114). Accordingly, the availability of nucleic acid sequences encoding all or a portion of this enzyme would facilitate studies to better understand the de novo synthesis of ceramide, provide genetic tools for the manipulation of this biosynthetic pathway, and provide a means to control sphingolipid concentration in plant cells.

SUMMARY OF THE INVENTION

The instant invention pertains to an isolated nucleic acid fragment encoding an Lcb1 subunit of serine palmitoyltransferase. In addition, this invention relates to a nucleic acid fragment that is complementary to the nucleic acid fragment encoding an Lcb1 subunit of serine palmitoyltransferase.

An additional embodiment of the instant invention pertains to a polypeptide encoding all or a substantial portion of an Lcb1 subunit of serine palmitoyltransferase.

In another embodiment, the instant invention relates to a chimeric gene encoding an Lcb1 subunit of serine palmitoyltransferase, or to a chimeric gene that comprises a nucleic acid fragment that is complementary to a nucleic acid fragment encoding an Lcb1 subunit of serine palmitoyltransferase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an Lcb1 subunit of serine palmitoyltransferase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an Lcb1 subunit of serine palmitoyltransferase in a transformed host cell comprising: a) transforming a host cell with a chimeric gene comprising a nucleic acid fragment encoding an Lcb1 subunit of serine palmitoyltransferase; and b) growing the transformed host cell under conditions that are suitable for expression of the chimeric gene wherein expression of the chimeric gene results in production of altered levels of the Lcb1 subunit of serine palmitoyltransferase in the transformed host cell.

An addition embodiment of the instant invention concerns a method for obtaining a nucleic acid fragment encoding all or a substantial portion of an amino acid sequence encoding an Lcb1 subunit of serine palmitoyltransferase.

A further embodiment of the instant invention is a method for evaluating at least one compound for its ability to inhibit the activity of a serine palmitoyltransferase Lcb1 subunit, the method comprising the steps of: (a) transforming a host cell with a chimeric gene comprising a nucleic acid fragment encoding a serine palmitoyltransferase Lcb1 subunit, operably linked to suitable regulatory sequences; (b) growing the transformed host cell under conditions that are suitable for expression of the chimeric gene wherein expression of the chimeric gene results in production of serine palmitoyltransferase Lcb1 subunit in the transformed host cell; (c) optionally purifying the serine palmitoyltransferase Lcb1 subunit expressed by the transformed host cell; (d) treating the serine palmitoyltransferase Lcb1 subunit with a compound to be tested; and (e) comparing the activity of the serine palmitoyltransferase Lcb1 subunit that has been treated with a test compound to the activity of an untreated serine palmitoyltransferase Lcb1 subunit, thereby selecting compounds with potential for inhibitory activity.

BRIEF DESCRIPTION OF THE DRAWING AND SEQUENCE DESCRIPTIONS

The invention can be more fully understood from the following detailed description and the accompanying drawing and Sequence Listing which form a part of this application.

FIG. 1 shows an alignment of the amino acid sequences from *Arabidopsis thaliana* serine palmitoyltransferase Lcb1 subunit (SEQ ID NO:13), the instant corn Lcb1 subunit of serine palmitoyltransferase (contig of cco1n.pk060.d3, ceb3.pk0002.d5, p0010.cbpaa34rb, p0010.cbpad89rb and cr1n.pk0001.e6; SEQ ID NO:2), the instant corn Lcb1 subunit of serine palmitoyltransferase (clone cen3n.pk0067.a2; SEQ ID NO:4) and the instant wheat Lcb1 subunit of serine palmitoyltransferase (clone wlm4.pk0022.f3; SEQ ID NO:12). Dashes are used by the program to maximize alignment of the sequences.

The following sequence descriptions and Sequence Listing attached hereto comply with the rules governing nucleotide and/or amino acid sequence disclosures in patent applications as set forth in 37 C.F.R. §1.821-1.825.

SEQ ID NO:1 is the nucleotide sequence comprising the contig assembled from the entire cDNA insert in clones ceb3.pk0002.d5 and cr1n.pk0001.e6 and a portion of the cDNA insert in clones cco1n.pk060.d3, p0010.cbpaa34rb and p0010.cbpad89rb encoding an entire corn serine palmitoyltransferase Lcb1 subunit homolog.

SEQ ID NO:2 is the deduced amino acid sequence of an entire corn serine palmitoyltransferase Lcb1 subunit homolog derived from the nucleotide sequence of SEQ ID NO:1.

SEQ ID NO:3 is the nucleotide sequence comprising the entire cDNA insert in clone cen3n.pk0067.a2 encoding a portion of a corn serine palmitoyltransferase Lcb1 subunit homolog.

SEQ ID NO:4 is the deduced amino acid sequence of a portion of a corn serine palmitoyltransferase Lcb1 subunit homolog derived from the nucleotide sequence of SEQ ID NO:3.

SEQ ID NO:5 is the nucleotide sequence comprising a portion of the cDNA insert in clone rca1n.pk009.h2 encoding a portion of a rice serine palmitoyltransferase Lcb1 subunit homolog.

SEQ ID NO:6 is the deduced amino acid sequence of a portion of a rice serine palmitoyltransferase Lcb1 subunit homolog derived from the nucleotide sequence of SEQ ID NO:5.

SEQ ID NO:7 is the nucleotide sequence comprising a portion of the cDNA insert in clone rls12.pk0012.d2 encoding a portion of a rice serine palmitoyltransferase Lcb1 subunit homolog.

SEQ ID NO:8 is the deduced amino acid sequence of a portion of a rice serine palmitoyltransferase Lcb1 subunit homolog derived from the nucleotide sequence of SEQ ID NO:7.

SEQ ID NO:9 is the nucleotide sequence comprising a portion of the cDNA insert in clone srr1c.pk002.k24 encoding a portion of a soybean serine palmitoyltransferase Lcb1 subunit homolog.

SEQ ID NO:10 is the deduced amino acid sequence of a portion of a soybean serine palmitoyltransferase Lcb1 subunit homolog derived from the nucleotide sequence of SEQ ID NO:9.

SEQ ID NO:11 is the nucleotide sequence comprising the entire cDNA insert in clone wlm4.pk0022.f3 encoding a portion of a wheat serine palmitoyltransferase Lcb1 subunit homolog.

SEQ ID NO:12 is the deduced amino acid sequence of a portion of a wheat serine palmitoyltransferase Lcb1 subunit homolog derived from the nucleotide sequence of SEQ ID NO:11.

SEQ ID NO:13 is the amino acid sequence of a *Arabidopsis thaliana* serine palmitoyltransferase Lcb1 subunit having an NCBI General Identifier No. 4006914.

The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the *Biochemical Journal* 219 (*No.* 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragment that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, substantially similar nucleic acid fragments may also be characterized by their ability to hybridize, under stringent conditions (0.1× SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the Lcb1 subunit of serine palmitoyltransferase proteins as set forth in SEQ ID NOs:2, 4, 6, 8, 10 and 12. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raiklhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature(London)* 327:70-73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several Lcb1 subunits of serine palmitoyltransferase have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Lcb1 Subunit of Serine Palmitoyltransferase

| Enzyme | Clone | Plant |
|---|---|---|
| Lcb1 Subunit of Serine Palmitoyltransferase | Contig of: ccoln.pk060.d3 ceb3.pk0002.d5 p0010.cbpaa34rb p0010.cbpad89rb cr1n.pk0001.e6 | Corn |
| | cen3n.pk0067.a2 | Corn |
| | rca1n.pk009.h2 | Rice |
| | rls12.pk0012.d2 | Rice |
| | srr1c.pk002.k24 | Soybean |
| | w1m4.pk0022.f3 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other serine palmitoyltransferase Lcb1 subunits, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *Proc. Natl. Acad Sci. USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed serine palmitoyltransferase Lcb1 subunits are present at higher or lower levels than normal or in cell types or developmental stages in which they are not normally found. This would have the effect of altering the level of sphingolipid biosynthesis in those cells. Because sphingolipids are involved in dissection stress tolerance overexpression of the Lcb1 subunit in transgenic plants will enhance stress tolerance in these plants. Manipulation of the levels of Lcb1 will lead to a greater accumulation of ceramides which are useful in the cosmetic industry.

Overexpression of the serine palmitoyltransferase Lcb1 subunit proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant serine palmitoyltransferase Lcb1 subunit to different cellular compartments, or to facilitate its secretion from the cell. It is thus envisioned that the chimeric gene described above may be further supplemented by altering the coding sequence to encode serine palmitoyltransferase Lcb1 subunit with appropriate intracellular targeting sequences such as transit sequences (Keegstra, K. (1989) *Cell* 56:247-253), signal sequences or sequences encoding endoplasmic reticulum localization (Chrispeels, J. J., (1991) *Ann. Rev. Plant Phys. Plant Mol. Biol* 42:21-53), or nuclear localization signals (Raikhel, N. (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding serine palmitoyltransferase Lcb1 subunit in plants for some applications. In order to accomplish this, a chimeric gene designed for co-suppression of the instant serine palmitoyltransferase Lcb1 subunit can be constructed by linking a gene or gene fragment encoding an serine palmitoyltransferase Lcb1 subunit to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant serine palmitoyltransferase Lcb1 subunit (or portions thereof) may be produced in heterologous host cells, particularly in the cells of microbial hosts, and can be used to prepare antibodies to the these proteins by methods well known to those skilled in the art. The antibodies are useful for detecting serine palmitoyltransferase Lcb1 subunit in situ in cells or in vitro in cell extracts. Preferred heterologous host cells for production of the instant serine palmitoyltransferase Lcb1 subunit are microbial hosts. Microbial expression systems and expression vectors containing regulatory sequences that direct high level expression of foreign proteins are well known to those skilled in the art. Any of these could be used to construct a chimeric gene for production of the instant serine palmitoyltransferase Lcb1 subunit. This chimeric gene could then be introduced into appropriate microorganisms via transformation to provide high level expression of the encoded serine palmitoyltransferase Lcb1 subunit. An example of a vector for high level expression of the instant serine palmitoyltransferase Lcb1 subunit in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) Genomics 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) Am. J. Hum. Genet. 32:314-331).

The production and use of plant gene-derived probes for use in genetic mapping is described in R. Bernatzky, R. and Tanksley, S. D. (1986) Plant Mol. Biol. Reporter 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: Nonmammalian Genomic Analysis: A Practical Guide, Academic press 1996, pp. 319-346, and references cited therein).

In another embodiment, nucleic acid probes derived from the instant nucleic acid sequences may be used in direct fluorescence in situ hybridization (FISH) mapping (Trask, B. J. (1991) Trends Genet. 7:149-154). Although current methods of FISH mapping favor use of large clones (several to several hundred KB; see Laan, M. et al. (1995) Genome Research 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) J. Lab. Clin. Med. 114(2):95-96), polymorphism of PCR-amplified fragments (CAPS; Sheffield, V. C. et al. (1993) Genomics 16:325-332), allele-specific ligation (Landegren, U. et al. (1988) Science 241:1077-1080), nucleotide extension reactions (Sokolov, B. P. (1990) Nucleic Acid Res. 18:3671), Radiation Hybrid Mapping (Walter, M. A. et al. (1997) Nature Genetics 7:22-28) and Happy Mapping (Dear, P. H. and Cook, P. R. (1989) Nucleic Acid Res. 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) Proc. Natl. Acad. Sci USA 86:9402; Koes et al., (1995) Proc. Natl. Acad. Sci USA 92:8149; Bensen et al., (1995) Plant Cell 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the serine palmitoyltransferase Lcb1 subunit. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a serine palmitoyltransferase Lcb1 subunit can be identified and obtained. This mutant plant can then be used to determine or confirm the natural function of the serine palmitoyltransferase Lcb1 subunit gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| eco1n | Corn Cob of 67 Day Old Plants Grown in Green House* | cco1n.pk060.d3 |
| ceb3 | Corn Embryo 20 Days After Pollination | ceb3.pk0002.d5 |
| cen3n | Corn Endosperm 20 Days After Pollination* | cen3n.pk0067.a2 |
| cr1n | Corn Root From 7 Day Old Seedlings* | cn1n.pk0001.e6 |
| p0010 | Log Phase Suspension Cells (BMS) Treated With A23187** | p0010.cbpaa34rb p0010.cbpad89rb |
| rca1n | Rice Callus* | rca1n.pk009.h2 |
| r1r12 | Rice Leaf 15 Days After Germination, 12 Hours After Infection of Strain *Magaporthe grisea* 4360-R-62 (AVR2-YAMO); Resistant | r1s12.pk0012.d2 |
| srr1c | Soybean 8-Day-Old Root | srr1c.pk002.k24 |
| w1m4 | Wheat Seedlings 4 Hours After Inoculation With *Erysiphe graminis f. sp tritici* | w1m4.pk0022.f3 |

*These libraries were normalized essentially as described in U.S. Pat. No. 5,482,845
**A23187 is Calbiochem catalog No. 100105.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding serine palmitoyltransferase Lcb1 subunits were identified by conducting BLAST (Basic Local Alignment Search Tool; Altschul, S. F., et al., (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Serine Palmitoyltransferase Lcb1 Subunit The BLASTX search using the EST sequences from several corn, rice, soybean and wheat clones revealed similarity of the proteins encoded by the cDNAs to serine palmitoyltransferase Lcb1 subunit from several *Arabidopsis thaliana* and *Homo sapiens*. The *Arabidopsis thaliana* sequence has GenBank Accession No. Z99708 while the *Homo sapiens* sequence has GenBank Accession No. Y08685. In the process of comparing the corn ESTs it was found that clones cbn10.pk0005.h3, cepe7.pk0018.h4, cr1n.pk0184.f3, cs1.pk0009.h4 and csi1n.pk0021.c3 have overlapping regions of homology. Comparing the corn ESTs revealed that clones cr1n.pk0001.e6, cepe7.pk0019.a4, cco1n.pk0013.a5 and cen3n.pk0134.h12 have overlapping regions of homology. Lastly, a comparison of the wheat ESTs from clones w1m4.pk0022.f3 and wre1n.pk0031.g5 revealed that they have overlapping regions of homology. Using this homology it was possible to align the ESTs and assemble contigs (a contig is an assemblage of overlapping nucleic acid sequences to form one contiguous nucleotide sequence). The individual sequences were assembled into unique contiguous nucleotide sequences encoding unique corn and wheat serine palmitoyltransferase Lcb1 subunits. The database accession numbers and BLAST results for each of these ESTs and contigs are shown in Table 3:

TABLE 3

BLAST Results for Clones Encoding Polypeptides Homologous to Serine Palmitoyltransferase Lcb1 Subunit

| Clone | GenBank Accession No. | Blast Score pLog |
|---|---|---|
| Contig of clones: cbn10.pk0005.h3 cepe7.pk0018.h4 cr1n.pk0184.f3 cs1.pk0009.h4 csi1n.pk0021.c3 | Y08685 | 8.00 |
| Contig of clones: cr1n.pk0001.e6 cepe7.pk0019.a4 cco1n.pk0013.a5 cen3n.pk0134.h12 | Z99708 | 57.52 |
| ceb3.pk0002.d5 | Y08685 | 36.70 |
| cr1n.pk0196.h6 | Z99708 | 28.30 |
| cen3n.pk0067.a2 | Z99708 | 22.51 |
| rca1n.pk009.h2 | Z99708 | 14.70 |
| srr1c.pk002.k24 | Z99708 | 27.70 |
| Contig of clones: w1m4.pk0022.f3 wre1n.pk0031.g5 | Y08685 | 49.30 |

The sequence from the entire cDNA insert in clones ceb3.pk0002.d5 and cr1n.pk0001.e6 was determined and a contig assembled with these sequences and the sequences from portions of the cDNA inserts in clones cco1n.p060.d3, p0010.cbpaa34rb and p0010.cbpad89rb. The nucleotide sequence of this contig is shown in SEQ ID NO:1; the deduced amino acid sequence of this cDNA is shown in SEQ ID NO:2. The nucleotide sequence set forth in SEQ ID NO:1 includes the EST sequences from clones cbn10.pk0005.h3, cepe7.pk0018.h4, cr1n.pk0184.f3, cs1.pk0009.h4, csi1n.pk0021.c3, cepe7.pk0019.a 4, cco1n.pk 0013.a5 and cen3n.pk0134.h12. The amino acid sequence set forth in SEQ ID NO:2 was evaluated by BLASTP, yielding a pLog value of >254 versus the *Arabidopsis thaliana* sequence (NCBI General Identifier No. 4006914). The sequence of the entire cDNA insert in clone cen3n.pk0067.a2 was determined and is shown in SEQ ID NO:3; the deduced amino acid sequence of this cDNA is shown in SEQ ID NO:4. The nucleotide sequence set forth in SEQ ID NO:3 includes the EST sequence from clone cr1n.pk0196.h6. The amino acid sequence set forth in SEQ ID NO:4 was evaluated by BLASTP, yielding a pLog value of 102.0 versus the *Arabidopsis thaliana* sequence. The sequence of a portion of the cDNA insert from clone rca1n.pk009.h2 is shown in SEQ ID NO:5; the deduced amino acid sequence of this cDNA is shown in SEQ ID NO:6. The sequence of a portion of the cDNA insert from clone rls12.pk0012.d2 is shown in SEQ ID NO:7; the deduced amino acid sequence of this cDNA is shown in SEQ ID NO:8. The sequence of a portion of the cDNA insert from clone srr1c.pk002.k24 is shown in SEQ ID NO:9; the deduced amino acid sequence of this cDNA is shown in SEQ ID NO:10. The sequence of the entire cDNA insert in clone wlm4.pk0022.f3 was determined and is shown in SEQ ID NO:11; the deduced amino acid sequence of this cDNA is shown in SEQ ID NO:12. The nucleotide sequence set forth in SEQ ID NO:11 includes the EST sequence from clone wre1n.pk0031.g5. The amino acid sequence set forth in SEQ ID NO:12 was evaluated by BLASTP, yielding a pLog value of 79.70 versus the *Arabidopsis thaliana* sequence.

FIG. 1 presents an alignment of the amino acid sequences set forth in SEQ ID NO:2, SEQ ID NO:4, SEQ ID NO:12 and the *Arabidopsis thaliana* sequence (SEQ ID NO:13). From this alignment it is clear that there are two types of serine palmitoyltransferase subunits in corn. One type has a similar structural arrangement to the *Arabidopsis thaliana* serine palmitoyl transferase Lcb1 subunit while the other type, represented by SEQ ID NO:4, has two deletions relative to SEQ ID NO:2 and the *Arabidopsis thaliana* sequence. The first deletion corresponds to amino acids 69-99 in SEQ ID NO:2 and the second deletion corresponds to amino acids 308 to 398 in SEQ ID NO:2. This type of corn serine palmitoyltransferase Lcb1 subunit also appears to be missing the C-terminal 31 amino acids with respect to the *Arabidopsis thaliana* sequence and the other corn sequence of the present invention. The amino acid sequences set forth in SEQ ID NO:2, SEQ ID NO:4 and SEQ ID NO:12 are 65.5, 61.5 and 62.4% similar to the *Arabidopsis thaliana* sequence.

Sequence alignments and percent similarity calculations were performed using the Megalign program of the LASARGENE bioinformatics computing suite (DNASTAR Inc., Madison, Wis.). Multiple alignment of the amino acid sequences and percent similarity calculations were performed using the Clustal method of alignment (Higgins, D. G. and Sharp, P. M. (1989) *CABIOS.* 5:151-153) using the default parameters (GAP PENALTY=10, GAP LENGTH PENALTY=10).

Sequence alignments and BLAST scores and probabilities indicate that the instant nucleic acid fragments encode two different, entire or nearly entire corn homologs of the Lcb1 subunit of serine palmitoyltransferase and portions of rice, soybean and wheat serine palmitoyltransferase homologs. These sequences represent the first corn, rice, soybean and wheat sequences encoding the Lcb1 subunit of serine palmitoyltransferase.

Example 4

Expression of Chimeric Genes in Monocot Cells

A chimeric gene comprising a cDNA encoding the Lcb1 subunit of serine palmitoyltransferase in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U. S. Biochemical). The resulting plasmid construct would comprise a chimeric gene encoding, in the 5' to 3' direction, the maize 27 kD zein promoter, a cDNA fragment encoding the Lcb1 subunit from serine palmitoyltransferase, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant serine palmitoyltransferase Lcb1 subunit in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding an Lcb1 subunit of serine palmitoyltransferase. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the Lcb1 subunit from serine palmitoyltransferase and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant serine palmitoyltransferase Lcb1 subunit can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the Lcb1 subunit from serine palmitoyltransferase are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride.

A small amount of 1 nun glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for their Ability to Inhibit the Activity of the Serine Palmitoyltransferase Lcb1 Subunit The serine palmitoyltransferase Lcb1 subunits described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant serine palmitoyltransferase Lcb1 subunits may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant serine palmitoyltransferase Lcb1 subunits, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the serine palmitoyltransferase Lcb1 subunits are expressed as fusion proteins, the purification protocol may include the use of an affinity resin which is specific for the fusion protein tag attached to the expressed enzyme or an affinity resin containing ligands which are specific for the enzyme. For example, a serine palmitoyltransferase Lcb1 subunit may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired.

Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the serine palmitoyltransferase Lcb1 subunit disclosed herein. Assays may be conducted under well known experimental conditions which permit optimal enzymatic activity. For example, assays for serine palmitoyltransferase Lcb1 subunit are presented by Hanada K. et al. (1997) J Biol Chem 272:32108-32114.

What is claimed is:

1. An isolated polynucleotide comprising:
   (a) a nucleotide sequence encoding a polypeptide having serine palmitoyltransferase Lcb1 subunit activity, wherein the amino acid sequence of the polypeptide and the amino acid sequence of SEQ ID NO:2 have at least 90% similarity based on the Clustal alignment method; or
   (b) the complement of the nucleotide sequence.

2. The polynucleotide of claim 1, wherein the amino acid sequence of the polypeptide and the amino acid sequence of SEQ ID NO:2 have at least 95% sequence similarity based on the Clustal alignment method.

3. The polynucleotide of claim 1, wherein the nucleotide sequence comprises the nucleotide sequence of SEQ ID NO:1.

4. The polynucleotide of claim 1, wherein the amino acid sequence of the polypeptide comprises the amino acid sequence of SEQ ID NO:2.

5. A vector comprising the polynucleotide of claim 1.

6. A chimeric gene comprising the polynucleotide of claim 1.

7. A method for transforming a cell comprising transforming a cell with the polynucleotide of claim 1.

8. A cell comprising the chimeric gene of claim 6, wherein the cell is selected from the group consisting of: a plant cell, a bacterial cell, a yeast cell and an insect cell.

9. A plant comprising the chimeric gene of claim 6.

10. A method for producing a plant comprising transforming a plant cell with the polynucleotide of claim 1 and regenerating a plant from the transformed plant cell.

11. A seed comprising the chimeric gene of claim 6.

* * * * *

UNITED STATES PATENT AND TRADEMARK OFFICE
CERTIFICATE OF CORRECTION

PATENT NO.        : 7,659,450 B2                                            Page 1 of 1
APPLICATION NO.   : 10/309629
DATED             : February 9, 2010
INVENTOR(S)       : Cahoon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 773 days.

Signed and Sealed this

Thirtieth Day of November, 2010

David J. Kappos
*Director of the United States Patent and Trademark Office*

SEQUENCE LISTING

```
<160> NUMBER OF SEQ ID NOS: 13

<210> SEQ ID NO 1
<211> LENGTH: 2060
<212> TYPE: DNA
<213> ORGANISM: Zea mays
<220> FEATURE:
<221> NAME/KEY: unsure
<222> LOCATION: (289)

<400> SEQUENCE: 1
ggtgcatact cccgcgtccc gcctggctcc ggggtccatt cgtcgaccca tctccggcga      60
aagcttacct ctactaccac tgaagcgaag gcgtcacatc ggaagaattg tagctgtttg     120
tcctcctctt cccgacagcg cagagcggag atccgaccgg acctgggatc gattccttcc     180
cttttctcga ttctgggcgc taacggttcc tgagggaagc tcctggggac atggacatgg     240
cattgcccgt tgtgaatgcc acaacggcgg tgctcgcccg tgtctcggnt gcgttcaatg     300
ccccacttgc ccgtgcagtc gtcttcgggg tccatatcga tgggcacttg gtcgtgggaa     360
ggcttcttat tgcaatcaac gtgtttcagc tctccaggaa gagctacaaa ccaccaaaga     420
aaccacttac tgaaaaggag attgatgagc tatgtgatga gtgggagcca gagccgctat     480
gccctccagt caaggagggg gctcgaattg atactccaat gttggaaagt gccgctggac     540
cacatacgat tgttgatggt aaagaagttg tgaactttgc atcagcaaac tacctcagtt     600
taattggcaa cgaaaagatt attgattctt gcatcagttc attggagaaa tatggtgttg     660
gttcttgtgg tccatgtggc ttttatggaa caactgatgt ccatcttgac tgtgagtcaa     720
agatagctaa attttggggg actccagact ccattcttta ttcatatggg atttctacaa     780
tattcaatgt gatacctgcc ttctgtaaga aaggagatat catagtcgct gatgagggtg     840
ttcactgggc agtgacaaat ggtctccatc tatcaagaag cactgtggtg tacttcaagc     900
acaatgatat ggcttcactt gcaagcactt tggaaaaact tactcgtgga aataaacgtg     960
ctgaaaagat tagacgctac attgttgtag aatccattta ccagaattct ggccaaattg    1020 ccccccttgga tgaaatcgtc aggttgaagg agaaatatcg gttccgtgtt attctggagg    1080
agagccattc ttttggtgtg cttggcaagt ctgggcgtgg ccttgctgaa cattatggag    1140
ttcctattga aaaaattgat ataattactg ctggaatggg aaatgcatta gctaccgatg    1200
gtggattttg tacaggaagt gtcagagttg ttgatcatca gcgtctaagc agctctggat    1260 atgtttctc tgcatctctg ccaccttatc ttgccactgc tgctgtttct gctgtcaact    1320
acctggagca gaatcccgca gttcttgcaa atctaaggag caatattgct cttttgcata    1380
aagaattatc agatactcca gggctagaaa ttttcagcca tgtttttgtca cctattgtct    1440 tccttaagct gaagaaatcg acaggttctc ctaccactga cctagacctt cttgaaacta    1500
ttgctggcag ggtcttgaag gaagactcag ttctcattgt gacatcaaag aagtcaaatc    1560
tggataggtg caaactcccc gttggaatcc gcctgttttgt atcagctgga catactgaat    1620
```

-continued

```
ccgacatctc caggctttcc tcatccttga agcgagtttc tgcggcagtt ctttcagact    1680
gcttttgatc cacatcggat acccttgaag atgaaagcca tccattttct acgcactttg    1740
taccctagac cgtgtgtgtg tgtttggtaa atgtacataa cctgtacatt tctacatatt    1800
tatgaattca ccttgttgtc gtttataccc gtagtacatg ggattttttt ttttgtagaa    1860
cagtgatgtt ggagaatagt gcgtttgtgc tgtacatctc gttgatttcc atgtagtgat    1920
gttttcccct gtatcctcac ccacaagaca ttggccgtct tatattttca aacaattgca    1980
acacccacct ctgctgtgtt gttaattaga ctcataacat acaaacttgt ccgtgcaaaa    2040
taaaaggggg ggccgtacac                                                 2060
```

<210> SEQ ID NO 2
<211> LENGTH: 485
<212> TYPE: PRT
<213> ORGANISM: Zea mays
<220> FEATURE:
<221> NAME/KEY: UNSURE
<222> LOCATION: (20)

<400> SEQUENCE: 2

```
Met Asp Met Ala Leu Pro Val Val Asn Ala Thr Thr Ala Val Leu Ala
  1               5                  10                  15

Arg Val Ser Xaa Ala Phe Asn Ala Pro Leu Ala Arg Ala Val Val Phe
             20                  25                  30

Gly Val His Ile Asp Gly His Leu Val Val Gly Arg Leu Leu Ile Ala
         35                  40                  45

Ile Asn Val Phe Gln Leu Ser Arg Lys Ser Tyr Lys Pro Pro Lys Lys
     50                  55                  60

Pro Leu Thr Glu Lys Glu Ile Asp Glu Leu Cys Asp Glu Trp Glu Pro
 65                  70                  75                  80

Glu Pro Leu Cys Pro Pro Val Lys Glu Gly Ala Arg Ile Asp Thr Pro
                 85                  90                  95

Met Leu Glu Ser Ala Ala Gly Pro His Thr Ile Val Asp Gly Lys Glu
            100                 105                 110

Val Val Asn Phe Ala Ser Ala Asn Tyr Leu Ser Leu Ile Gly Asn Glu
        115                 120                 125

Lys Ile Ile Asp Ser Cys Ile Ser Ser Leu Glu Lys Tyr Gly Val Gly
    130                 135                 140

Ser Cys Gly Pro Cys Gly Phe Tyr Gly Thr Thr Asp Val His Leu Asp
145                 150                 155                 160

Cys Glu Ser Lys Ile Ala Lys Phe Leu Gly Thr Pro Asp Ser Ile Leu
                165                 170                 175

Tyr Ser Tyr Gly Ile Ser Thr Ile Phe Asn Val Ile Pro Ala Phe Cys
            180                 185                 190

Lys Lys Gly Asp Ile Ile Val Ala Asp Glu Gly Val His Trp Ala Val
        195                 200                 205

Thr Asn Gly Leu His Leu Ser Arg Ser Thr Val Val Tyr Phe Lys His
    210                 215                 220

Asn Asp Met Ala Ser Leu Ala Ser Thr Leu Glu Lys Leu Thr Arg Gly
225                 230                 235                 240

Asn Lys Arg Ala Glu Lys Ile Arg Arg Tyr Ile Val Val Glu Ser Ile
                245                 250                 255

Tyr Gln Asn Ser Gly Gln Ile Ala Pro Leu Asp Glu Ile Val Arg Leu
            260                 265                 270

Lys Glu Lys Tyr Arg Phe Arg Val Ile Leu Glu Glu Ser His Ser Phe
```

```
                275                 280                 285
Gly Val Leu Gly Lys Ser Gly Arg Gly Leu Ala Glu His Tyr Gly Val
    290                 295                 300
Pro Ile Glu Lys Ile Asp Ile Ile Thr Ala Gly Met Gly Asn Ala Leu
305                 310                 315                 320
Ala Thr Asp Gly Gly Phe Cys Thr Gly Ser Val Arg Val Val Asp His
                325                 330                 335
Gln Arg Leu Ser Ser Ser Gly Tyr Val Phe Ser Ala Ser Leu Pro Pro
            340                 345                 350
Tyr Leu Ala Thr Ala Ala Val Ser Ala Val Asn Tyr Leu Glu Gln Asn
        355                 360                 365
Pro Ala Val Leu Ala Asn Leu Arg Ser Asn Ile Ala Leu Leu His Lys
    370                 375                 380
Glu Leu Ser Asp Thr Pro Gly Leu Glu Ile Phe Ser His Val Leu Ser
385                 390                 395                 400
Pro Ile Val Phe Leu Lys Leu Lys Lys Ser Thr Gly Ser Pro Thr Thr
                405                 410                 415
Asp Leu Asp Leu Leu Glu Thr Ile Ala Gly Arg Val Leu Lys Glu Asp
            420                 425                 430
Ser Val Leu Ile Val Thr Ser Lys Lys Ser Asn Leu Asp Arg Cys Lys
        435                 440                 445
Leu Pro Val Gly Ile Arg Leu Phe Val Ser Ala Gly His Thr Glu Ser
    450                 455                 460
Asp Ile Ser Arg Leu Ser Ser Ser Leu Lys Arg Val Ser Ala Ala Val
465                 470                 475                 480
Leu Ser Asp Cys Phe
                485

<210> SEQ ID NO 3
<211> LENGTH: 907
<212> TYPE: DNA
<213> ORGANISM: Zea mays

<400> SEQUENCE: 3
gcacgaggga ttttcaggt cacttggtcg tggaagggct tcttattgca gtcatagtgt    60
tccagctctc caggaagagt acaaaccac caaagaagcc actcactgaa agtgccgctg   120
gaccacatac gattgttgat ggtaaagaag ttgtgaactt tgcatcagca aactacctca   180
gtttaattgg caacgaaaag attattgatt cttgcatcag ttcattggag aaatatggtg   240
ttggttcttg tggtccatgt ggcttttatg aacaactga tgtccatctt gactgtgagt   300
caaagatagc taaattttg gggactccag actccattct ttattcatat ggatttcta   360 caatattcaa tgtgatacct gccttctgta agaaaggaga tcatagtc gctgatgagg   420 gtgttcactg gcagtgaca aatggtctcc atctatcaag aagcactgtg gtgtacttca   480
agcacaatga tatggcttca cttgcaagca ctttggaaaa acttactcgt ggaaataaac   540
gtgctgaaaa gattagacgc tacattgttg tagaatccat ttaccagaat tctggccaaa   600
ttgccccctt ggatgagatt gtcaggttga aggagaaata tcgattccgt gttattctgg   660
aggagagtca ttcttttggg gtgcttggca agtctgggcg tggccttgct gaacattatg   720
gagttcctgt gagtgtttgg cctcagcttt tcttaatgtt tcaccataat gccccacctg   780
tggtgtctga ccggggtgcg ttgttaccta gctcccaaac gaggcctaac tgtttggtga   840
aatgcttggg acaaagtggc catcaagaat ggagtcatgg aacatcagca ggacactaca   900
``` agaaaaa 907

<210> SEQ ID NO 4
<211> LENGTH: 301
<212> TYPE: PRT
<213> ORGANISM: Zea mays

<400> SEQUENCE: 4

```
Thr Arg Asp Phe Ser Gly His Leu Val Val Glu Gly Leu Leu Ile Ala
  1               5                  10                  15

Val Ile Val Phe Gln Leu Ser Arg Lys Ser Tyr Lys Pro Pro Lys Lys
             20                  25                  30

Pro Leu Thr Glu Ser Ala Ala Gly Pro His Thr Ile Val Asp Gly Lys
         35                  40                  45

Glu Val Val Asn Phe Ala Ser Ala Asn Tyr Leu Ser Leu Ile Gly Asn
     50                  55                  60

Glu Lys Ile Ile Asp Ser Cys Ile Ser Ser Leu Glu Lys Tyr Gly Val
 65                  70                  75                  80

Gly Ser Cys Gly Pro Cys Gly Phe Tyr Gly Thr Thr Asp Val His Leu
                 85                  90                  95

Asp Cys Glu Ser Lys Ile Ala Lys Phe Leu Gly Thr Pro Asp Ser Ile
            100                 105                 110

Leu Tyr Ser Tyr Gly Ile Ser Thr Ile Phe Asn Val Ile Pro Ala Phe
        115                 120                 125

Cys Lys Lys Gly Asp Ile Ile Val Ala Asp Glu Gly Val His Trp Ala
    130                 135                 140

Val Thr Asn Gly Leu His Leu Ser Arg Ser Thr Val Val Tyr Phe Lys
145                 150                 155                 160

His Asn Asp Met Ala Ser Leu Ala Ser Thr Leu Glu Lys Leu Thr Arg
                165                 170                 175

Gly Asn Lys Arg Ala Glu Lys Ile Arg Arg Tyr Ile Val Val Glu Ser
            180                 185                 190

Ile Tyr Gln Asn Ser Gly Gln Ile Ala Pro Leu Asp Glu Ile Val Arg
        195                 200                 205

Leu Lys Glu Lys Tyr Arg Phe Arg Val Ile Leu Glu Glu Ser His Ser
    210                 215                 220

Phe Gly Val Leu Gly Lys Ser Gly Arg Gly Leu Ala Glu His Tyr Gly
225                 230                 235                 240

Val Pro Val Ser Val Trp Pro Gln Leu Phe Leu Met Phe His His Asn
                245                 250                 255

Ala Pro Pro Val Val Ser Asp Arg Gly Ala Leu Leu Pro Ser Ser Gln
            260                 265                 270

Thr Arg Pro Asn Cys Leu Val Lys Cys Leu Gly Gln Ser Gly His Gln
        275                 280                 285

Glu Trp Ser His Gly Thr Ser Ala Gly His Tyr Lys Lys
    290                 295                 300
```

<210> SEQ ID NO 5
<211> LENGTH: 455
<212> TYPE: DNA
<213> ORGANISM: Oryza sativa
<220> FEATURE:
<221> NAME/KEY: unsure
<222> LOCATION: (263)
<220> FEATURE:
<221> NAME/KEY: unsure
<222> LOCATION: (290)
<220> FEATURE:

```
<221> NAME/KEY: unsure
<222> LOCATION: (347)
<220> FEATURE:
<221> NAME/KEY: unsure
<222> LOCATION: (374)
<220> FEATURE:
<221> NAME/KEY: unsure
<222> LOCATION: (396)
<220> FEATURE:
<221> NAME/KEY: unsure
<222> LOCATION: (449)

<400> SEQUENCE: 5
cttctcccct ctttgactcg ttttgcgccc aagtcgatcc ccaacgtctc ctcctcgctg      60
gttcgcccgc cgcgccgcgc cgatctccat ccgttccacg aagcagcggt gaccgggtgc     120
tgtcgtcctg ctccccgctt ccettccggc tccgatttga ggcgctaaag tttccattcc     180
gtgttacgaa aagctgcatt aggacatgga catggcattg ccaatagtga atgccaccgc     240
agcggtgctt gctcgtgtct canctgcatt caatgcccct tttgcccgcn cagttgtctt     300
tggggttcat atcgatgggc acctggttgt tgaagggctc cttatancgg tcataagtgt     360
ttcaagcttt ctangaagag ctacaaaccg cccaanaagc cactcaatga aaaggagatt     420
gacgagctat gtgatgaatg ggagccagna cctcc                                455

<210> SEQ ID NO 6
<211> LENGTH: 81
<212> TYPE: PRT
<213> ORGANISM: Oryza sativa
<220> FEATURE:
<221> NAME/KEY: UNSURE
<222> LOCATION: (18)
<220> FEATURE:
<221> NAME/KEY: UNSURE
<222> LOCATION: (27)
<220> FEATURE:
<221> NAME/KEY: UNSURE
<222> LOCATION: (46)
<220> FEATURE:
<221> NAME/KEY: UNSURE
<222> LOCATION: (51)
<220> FEATURE:
<221> NAME/KEY: UNSURE
<222> LOCATION: (55)
<220> FEATURE:
<221> NAME/KEY: UNSURE
<222> LOCATION: (62)
<220> FEATURE:
<221> NAME/KEY: UNSURE
<222> LOCATION: (80)

<400> SEQUENCE: 6

Met Ala Leu Pro Ile Val Asn Ala Thr Ala Ala Val Leu Ala Arg Val
 1               5                  10                  15

Ser Xaa Ala Phe Asn Ala Pro Phe Ala Arg Xaa Val Val Phe Gly Val
                20                  25                  30

His Ile Asp Gly His Leu Val Val Glu Gly Leu Leu Ile Xaa Val Ile
            35                  40                  45

Ser Val Xaa Lys Leu Ser Xaa Lys Ser Tyr Lys Pro Pro Xaa Lys Pro
        50                  55                  60

Leu Asn Glu Lys Glu Ile Asp Glu Leu Cys Asp Glu Trp Glu Pro Xaa
65                  70                  75                  80

Pro

<210> SEQ ID NO 7
<211> LENGTH: 567
```

-continued

```
<212> TYPE: DNA
<213> ORGANISM: Oryza sativa
<220> FEATURE:
<221> NAME/KEY: unsure
<222> LOCATION: (311)
<220> FEATURE:
<221> NAME/KEY: unsure
<222> LOCATION: (339)
<220> FEATURE:
<221> NAME/KEY: unsure
<222> LOCATION: (377)
<220> FEATURE:
<221> NAME/KEY: unsure
<222> LOCATION: (436)
<220> FEATURE:
<221> NAME/KEY: unsure
<222> LOCATION: (446)
<220> FEATURE:
<221> NAME/KEY: unsure
<222> LOCATION: (461)
<220> FEATURE:
<221> NAME/KEY: unsure
<222> LOCATION: (465)
<220> FEATURE:
<221> NAME/KEY: unsure
<222> LOCATION: (467)
<220> FEATURE:
<221> NAME/KEY: unsure
<222> LOCATION: (481)
<220> FEATURE:
<221> NAME/KEY: unsure
<222> LOCATION: (483)
<220> FEATURE:
<221> NAME/KEY: unsure
<222> LOCATION: (489)
<220> FEATURE:
<221> NAME/KEY: unsure
<222> LOCATION: (492)
<220> FEATURE:
<221> NAME/KEY: unsure
<222> LOCATION: (498)
<220> FEATURE:
<221> NAME/KEY: unsure
<222> LOCATION: (518)
<220> FEATURE:
<221> NAME/KEY: unsure
<222> LOCATION: (549)
<220> FEATURE:
<221> NAME/KEY: unsure
<222> LOCATION: (559)

<400> SEQUENCE: 7
gtaagaaagg agacatcata gttgctgatg aaggtgtgca ctgggcagtg caaaatggtc      60
ttcatctgtc aagaagcact gttgtttatt ttaaacacaa tgatatggct tcacttgcaa     120
acactttgga aaaacttaca cgtggaaata acgagcaga aaagatcaga cgatacattg     180
ttgtagaatc tatctaccag aattctggtc aaattgctcc cttggatgag attgtcagat     240
tgaaggagaa atatcgattc cgtgttattc tggaggaaac catcttttgg tgtgcttggc     300
cagtctggac naggccttgc tgaacattat ggattccant gagtacccct gacatttgtt     360
ctctcatcgc accaaantag aagattaaaa ggatagattg acaaattgat atacacgctg     420
gaatggggat gcattnctac gatggnggtt tgtcaggaag nttanantgt gtcacagctc     480
nancattcng cnagttcncg ctctcgcact atctgcancg cgcggtcgcg tcacactgag     540
ggacctcant ctgcaaccna gacaatt                                         567

<210> SEQ ID NO 8
<211> LENGTH: 110
<212> TYPE: PRT
<213> ORGANISM: Oryza sativa
<220> FEATURE:
```

```
<221> NAME/KEY: UNSURE
<222> LOCATION: (103)

<400> SEQUENCE: 8

Lys Lys Gly Asp Ile Ile Val Ala Asp Glu Gly Val His Trp Ala Val
  1               5                  10                  15

Gln Asn Gly Leu His Leu Ser Arg Ser Thr Val Val Tyr Phe Lys His
             20                  25                  30

Asn Asp Met Ala Ser Leu Ala Asn Thr Leu Glu Lys Leu Thr Arg Gly
         35                  40                  45

Asn Lys Arg Ala Glu Lys Ile Arg Arg Tyr Ile Val Val Glu Ser Ile
     50                  55                  60

Tyr Gln Asn Ser Gly Gln Ile Ala Pro Leu Asp Glu Ile Val Arg Leu
 65                  70                  75                  80

Lys Glu Lys Tyr Arg Phe Arg Val Ile Leu Glu Glu Pro Ser Phe Gly
                 85                  90                  95

Val Leu Gly Gln Ser Gly Xaa Gly Leu Ala Glu His Tyr Gly
                100                 105                 110

<210> SEQ ID NO 9
<211> LENGTH: 431
<212> TYPE: DNA
<213> ORGANISM: Glycine max

<400> SEQUENCE: 9
gcacgagctc ccactcgcca gcacaattga ttcgtcggta caacttgtcg tttagcacgt      60
tcatgttcat gtttgattcg tgtgttgcat tggttgata gtgttgcgga attttttaga     120
agtgtgaatg ttcgttcatg catgagcggc tcttaaagtt gccttgcgga ttcgattgcg     180
atatattgag actgcgatgg cctcagccgt cgtgaatttc ttgaacgcga cgttggattg     240
ggtgacgttt gcgtcggatg gtccttctgc gcgagctgta gttttcggag tccatatcgg     300
tggacatttg tttatcgaag tgttttttgct agttgtcata cttttcttgc tttcacagaa     360
aagttacaag cctcctaaaa ggcctttaac aaataaggaa attgatgagt tatgtgacga     420
atgggttcca t                                                          431

<210> SEQ ID NO 10
<211> LENGTH: 78
<212> TYPE: PRT
<213> ORGANISM: Glycine max

<400> SEQUENCE: 10

Met Ala Ser Ala Val Val Asn Phe Leu Asn Ala Thr Leu Asp Trp Val
  1               5                  10                  15

Thr Phe Ala Ser Asp Gly Pro Ser Ala Arg Ala Val Val Phe Gly Val
             20                  25                  30

His Ile Gly Gly His Leu Phe Ile Glu Val Phe Leu Leu Val Val Ile
         35                  40                  45

Leu Phe Leu Leu Ser Gln Lys Ser Tyr Lys Pro Pro Lys Arg Pro Leu
     50                  55                  60

Thr Asn Lys Glu Ile Asp Glu Leu Cys Asp Glu Trp Val Pro
 65                  70                  75

<210> SEQ ID NO 11
<211> LENGTH: 228
<212> TYPE: PRT
<213> ORGANISM: Triticum aestivum
```

<400> SEQUENCE: 11

```
Gln Asn Ser Gly Gln Ile Ala Pro Leu Asp Glu Ile Val Lys Leu Lys
  1               5                  10                  15

Glu Lys Tyr Leu Phe Arg Val Ile Leu Glu Glu Ser His Ser Phe Gly
             20                  25                  30

Val Leu Gly Lys Ser Gly Arg Gly Leu Ala Glu His Tyr Gly Val Pro
         35                  40                  45

Ile Asp Lys Ile Asp Ile Ile Thr Ala Gly Met Gly Asn Ala Leu Ala
     50                  55                  60

Thr Asp Gly Gly Phe Cys Thr Gly Ser Ala Arg Val Asp His Gln
 65                  70                  75                  80

Arg Leu Ser Ser Ala Gly Tyr Val Phe Ser Ala Ser Leu Pro Pro Tyr
                 85                  90                  95

Leu Ala Ser Ala Ala Val Ser Ala Val Asn Tyr Leu Glu Glu Asn Pro
            100                 105                 110

Ser Val Leu Ala Asn Leu Arg Ser Asn Val Ala Leu Leu His Ala Gly
            115                 120                 125

Leu Ser Asp Ala Pro Gly Leu Glu Ile Ser Ser His Ala Leu Ser Pro
        130                 135                 140

Ile Val Phe Leu Lys Leu Lys Lys Ser Thr Gly Ser Leu Ala Thr Asp
145                 150                 155                 160

Leu Asp Leu Leu Glu Thr Ile Ala Glu Gln Val Leu Lys Glu Asp Ser
                165                 170                 175

Val Phe Ile Val Ala Ser Lys Arg Ser Thr Leu Asp Arg Cys Lys Leu
            180                 185                 190

Pro Val Gly Ile Arg Leu Phe Val Ser Ala Gly His Thr Glu Ser Asp
        195                 200                 205

Ile Ser Lys Val Cys Ser Ser Leu Lys Arg Ile Ser Ala Ser Val Leu
    210                 215                 220

Ser Asp His Val
225
```

<210> SEQ ID NO 12
<211> LENGTH: 56
<212> TYPE: PRT
<213> ORGANISM: Triticum aestivum

<400> SEQUENCE: 12

```
Met Ala Leu Pro Val Val Asn Ala Thr Ala Ala Val Leu Ala Arg Val
  1               5                  10                  15

Ser Ala Ala Phe Asn Gly Pro Leu Ala Arg Ala Val Val Phe Gly Val
             20                  25                  30

His Ile Asp Gly His Leu Val Glu Arg Leu Leu Ile Ala Val Lys
         35                  40                  45

Val Phe Gln Leu Ser Arg Lys Ser
     50                  55
```

<210> SEQ ID NO 13
<211> LENGTH: 475
<212> TYPE: PRT
<213> ORGANISM: Arabidopsis thaliana

<400> SEQUENCE: 13

```
Met Ala Ser Asn Leu Val Glu Met Phe Asn Ala Ala Leu Asn Trp Val
  1               5                  10                  15

Thr Met Ile Leu Glu Ser Pro Ser Ala Arg Val Val Leu Phe Gly Val
```

```
            20                  25                  30
Pro Ile Arg Gly His Phe Phe Val Glu Gly Leu Leu Gly Val Val Ile
            35                  40                  45
Ile Ile Leu Leu Thr Arg Lys Ser Tyr Lys Pro Pro Lys Arg Pro Leu
            50                  55                  60
Thr Glu Gln Glu Ile Asp Glu Leu Cys Asp Glu Trp Val Pro Glu Pro
65                  70                  75                  80
Leu Ile Pro Pro Ile Thr Glu Asp Met Lys His Glu Pro Pro Val Leu
                85                  90                  95
Glu Ser Ala Ala Gly Pro His Thr Thr Val Asn Gly Lys Asp Val Val
                100                 105                 110
Asn Phe Ala Ser Ala Asn Tyr Leu Gly Leu Ile Gly His Glu Lys Leu
            115                 120                 125
Leu Glu Ser Cys Thr Ser Ala Leu Glu Lys Tyr Gly Val Gly Ser Cys
            130                 135                 140
Gly Pro Arg Gly Phe Tyr Gly Thr Ile Asp Val His Leu Asp Cys Glu
145                 150                 155                 160
Thr Arg Ile Ser Lys Phe Leu Gly Thr Pro Asp Ser Ile Leu Tyr Ser
                165                 170                 175
Tyr Gly Leu Ser Thr Met Phe Ser Thr Ile Pro Cys Phe Cys Lys Lys
                180                 185                 190
Gly Asp Val Ile Val Ala Asp Glu Gly Val His Trp Gly Ile Gln Asn
                195                 200                 205
Gly Leu Gln Leu Ser Arg Ser Thr Ile Val Tyr Phe Lys His Asn Asp
            210                 215                 220
Met Glu Ser Leu Arg Ile Thr Leu Glu Lys Ile Met Thr Lys Tyr Lys
225                 230                 235                 240
Arg Ser Lys Asn Leu Arg Arg Tyr Ile Val Ala Glu Ala Val Tyr Gln
                245                 250                 255
Asn Ser Gly Gln Ile Ala Pro Leu Glu Ile Val Lys Leu Lys Glu
                260                 265                 270
Lys Tyr Arg Phe Arg Val Ile Leu Asp Glu Ser Asn Ser Phe Gly Val
            275                 280                 285
Leu Gly Arg Ser Gly Arg Gly Leu Ala Glu His His Ser Val Pro Ile
            290                 295                 300
Glu Lys Ile Asp Val Val Thr Ala Ala Met Gly His Ala Leu Ala Thr
305                 310                 315                 320
Glu Gly Gly Phe Cys Thr Gly Asn Ala Arg Ile Ile Asp Tyr Gln Arg
                325                 330                 335
Leu Ser Ser Ser Gly Tyr Val Phe Ser Ala Ser Leu Pro Pro Tyr Leu
            340                 345                 350
Ala Ser Ala Ala Ile Thr Ala Ile Asp Val Ile Asp Gln Asn Pro Asp
            355                 360                 365
Ile Asn Ala Gly Asn Asn Ala Gly Leu Ser Asp Ile Lys Gly Met Ser
            370                 375                 380
Leu Thr Ser Asn Arg Glu Ser Pro Ile Val Phe Leu Lys Leu Glu Lys
385                 390                 395                 400
Ser Ser Gly Ser Ala Lys Asp Asp Leu Leu Leu Glu Lys Met Ala
                405                 410                 415
Asp Arg Ala Leu Lys Glu Asp Ser Leu Leu Val Val Ser Ser Lys Arg
            420                 425                 430
Ser Phe Leu Asp Lys Cys Arg Leu Pro Val Gly Ile Lys Leu Tyr Val
            435                 440                 445
```

-continued

```
Ser Ala Gly His Ser Glu Ser Asp Leu Leu Lys Ala Ser Glu Ser Leu
    450                 455                 460

Lys Arg Leu Ala Ser Glu Leu Leu Leu Lys Ser
465                 470                 475
```